United States Patent
Ge et al.

(10) Patent No.: US 8,953,104 B2
(45) Date of Patent: Feb. 10, 2015

(54) AUTOMATIC SHADING ELECTRIC WELDING LENS COMPRISING A LIQUID CRYSTAL PLATE AND A TIME-DELAY SWITCH

(75) Inventors: Xiangdong Ge, Hangzhou (CN); Senwen Wang, Hangzhou (CN)

(73) Assignee: Hangzhou Rainbow Electronic Co., Ltd., Hangzhou (CN)

( * ) Notice: Subject to any disclaimer, the term of this patent is extended or adjusted under 35 U.S.C. 154(b) by 447 days.

(21) Appl. No.: 13/079,120

(22) Filed: Apr. 4, 2011

(65) Prior Publication Data

US 2011/0176072 A1 Jul. 21, 2011

Related U.S. Application Data

(63) Continuation of application No. PCT/CN2010/070640, filed on Feb. 11, 2010.

(30) Foreign Application Priority Data

May 14, 2009 (CN) .......................... 2009 2 0119838

(51) Int. Cl.
*G02F 1/1335* (2006.01)
*A61F 9/06* (2006.01)
*G02F 1/1347* (2006.01)

(52) U.S. Cl.
CPC ............ *A61F 9/067* (2013.01); *G02F 1/13471* (2013.01)
USPC ........................................................ 349/14

(58) Field of Classification Search
CPC ...... G02F 1/13471; B23K 9/32; G02C 7/101; A61F 9/023; E06B 2009/2464

USPC .................................................. 349/13, 14, 16
See application file for complete search history.

(56) References Cited

U.S. PATENT DOCUMENTS

| | | | |
|---|---|---|---|
| 6,340,234 B1 * | 1/2002 | Brown, Jr. | 362/105 |
| 7,029,136 B2 | 4/2006 | Hsu | |
| 2006/0203148 A1 * | 9/2006 | Magnusson et al. | 349/96 |

FOREIGN PATENT DOCUMENTS

| | | |
|---|---|---|
| CN | 2894663 | 5/2007 |
| CN | 201019914 | 2/2008 |
| CN | 201061582 | 5/2008 |
| CN | 201200542 | 3/2009 |
| RU | 91616 | 2/2010 |

OTHER PUBLICATIONS

2011117258, Jun. 28, 2012, Russian Decision on Grant.

* cited by examiner

*Primary Examiner* — Paul Lee
(74) *Attorney, Agent, or Firm* — Workman Nydegger

(57) ABSTRACT

An automatic shading electric welding lens comprises a view window and a side frame. The view window is composed of an optical filter and a liquid crystal sheet sequentially overlapped. The automatic shading electric welding lens is provided with an illuminating device. The illuminating device includes a lighting body, a switch and a power supply electrically connected to each other to form a loop. The lighting body is arranged on a surface of the side frame facing a welding object. The lighting body is a light emitting diode. The switch is a time-delay switch.

6 Claims, 2 Drawing Sheets

AUTOMATIC SHADING ELECTRIC WELDING LENS COMPRISING A LIQUID CRYSTAL PLATE AND A TIME-DELAY SWITCH

CROSS-REFERENCE TO RELATED APPLICATIONS

The present application is a Continuation of international of Patent Application No. PCT/CN2010/070640, entitled "AUTOMATIC SHADING ELECTRIC WELDING LENS" and filed on Feb. 11, 2010, which claims priority to Chinese Patent Application No. 200920119838.7, entitled "AUTOMATIC SHADING ELECTRIC WELDING LENS" and filed on May 14, 2009. The preceding applications are each incorporated herein by reference in their entirety.

FIELD OF THE INVENTION

The invention relates to an auto-darkening welding lens, and in particular to an auto-darkening welding lens that can be used under low ambient lighting conditions.

BACKGROUND OF THE INVENTION

Auto-darkening welding lenses are able to adjust their darkening levels according to the welding arc, completely preventing electro-ophthalmia, an occupational disease among welders. So the welder can work with both his hands, auxiliary procedures for welding are cut, welding quality and efficiency are improved, and no-load power consumption of the welding machine is reduced. It can be seen that the auto-darkening welding lens is going to be the next leading welding protection product. However, the auto-darkening welding lens includes infrared-blocking and ultraviolet-blocking filters and two liquid crystal plates, resulting low light transmittance when not exposed to the welding arc; hence, the welder may have a hard time locating the welding point under low indoor lighting conditions or when the equipment is backlit, which may cause poor welds.

BRIEF SUMMARY

To resolve the drawbacks in the prior art, the present invention provides an auto-darkening welding lens, ensuring good welding quality and convenience under low ambient lighting conditions.

The technical solution of the invention includes:

An auto-darkening welding lens including a window and a frame, the window including a filter and a liquid crystal plate that are stacked in an order, wherein, the auto-darkening welding lens has a lighting device, the lighting device including a luminous element, a switch and a power supply that are electrically connected to form a loop, the luminous element being arranged on a face of the frame that is towards a welding object.

The luminous element is a light-emitting diode (LED).

The switch is a time-delay switch.

The time-delay switch includes a button, a capacitor for charging and discharging, a discharge resistor, a gate chip and a transistor. The button is connected at a terminal to a power supply terminal, and is connected at the other terminal to the capacitor. The capacitor is connected in parallel to the discharge resistor. The gate chip is connected at its input terminal to a voltage output terminal of the capacitor, and is connected at its output terminal to a base of the transistor. The transistor is connected at its emitter to the ground. The LED is connected at its cathode to a collector of the transistor, and is connected at its anode to the power supply terminal.

The gate chip is a 74HC14 chip.

The gate chip includes six NOT gates, with a NOT gate (A), a NOT gate (B), parallel-connected NOT gates (C and F) and parallel-connected NOT gates (D and E) connected in series in an order. The input terminal of the gate chip is an input terminal of the NOT gate (A), and the output terminal of the gate chip is output terminals of the parallel-connected NOT gates (D and E).

The discharge resistor includes two resistors connected in parallel.

The power supply terminal is connected in parallel to a decoupling capacitor.

The invention may bring the following advantages. 1) The lighting device allows for locating the welding site under low ambient lighting conditions and ensures welding quality. 2) Use of the time-delay switch can save electricity, and avoid the procedure of turning off the luminous element, making the auto darkening welding lens easier to use. 3) The CMOS gate chip, with low power consumption and high input impedance, is used, so that the capacitor in the charging and discharging circuit can have a low capacity, which may reduce the cost and lighten the weight. 4) Two resistors connected in parallel are used as the discharge resistor, permitting flexible adjustment of the discharge time.

DETAILED DESCRIPTION

The invention is described in details hereinafter with reference to the embodiments and drawings.

Figure 1:
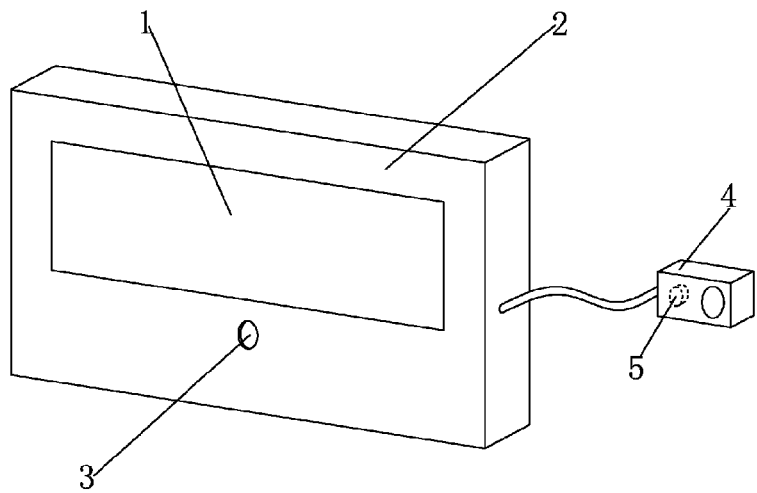
FIG. 1 is a structural diagram of the invention.

Refer to FIG. 1. An auto-darkening welding lens includes a window 1 and a frame 2. The window 1 includes a filter and a liquid crystal plate stacked in an order. A control chip, a photoelectric sensor and a solar cell that are electrically connected are arranged in the frame 2. As an improvement over the prior art, the invention further includes a lighting device. And the lighting device includes a luminous element 3, a switch 5 and a power supply 4 that are electrically connected to form a loop. The luminous element 3 is arranged on a face of the frame 2 that is towards the welding object. In an embodiment, the power supply 4 is a lithium battery, the luminous element is a light-emitting diode (LED), the switch is a time-delay switch, and the LED can turn off automatically after lighting up for a while.

Figure 2:
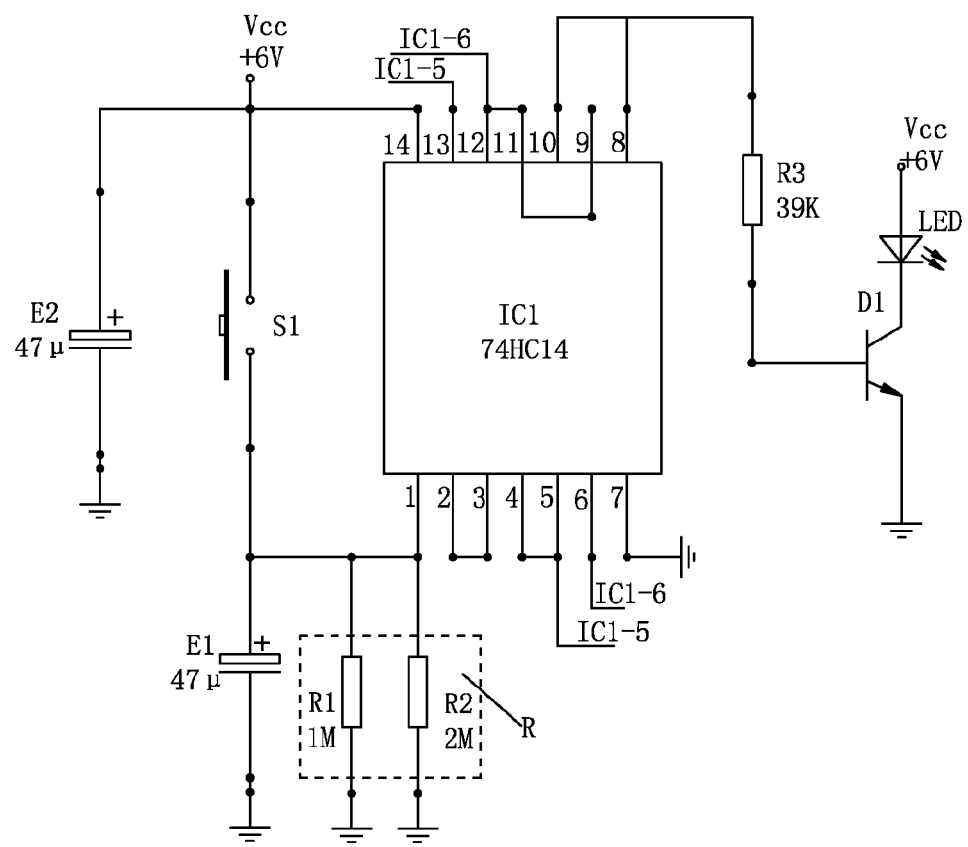
FIG. 2 is a circuit diagram of the time-delay switch.
Figure 3:
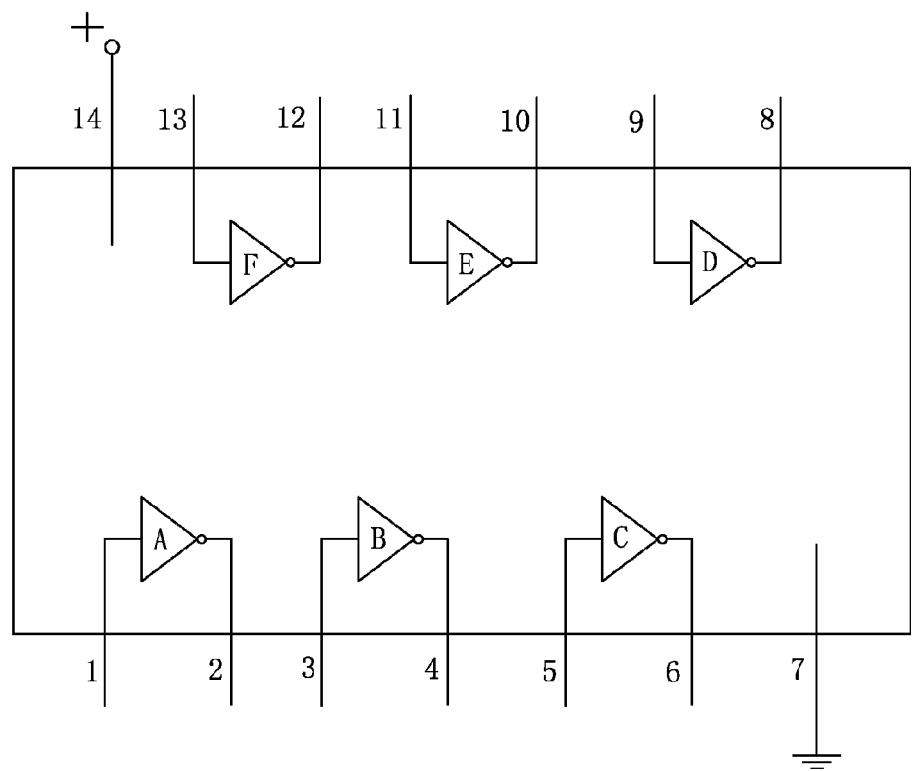
FIG. 3 illustrates the internal structure of the gate chip.
Figure 4:
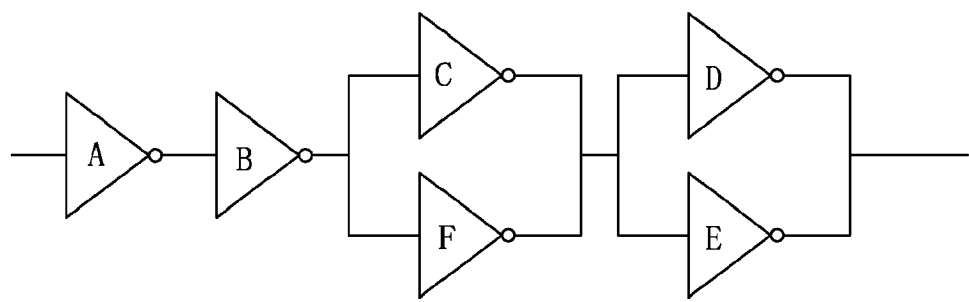
FIG. 4 illustrates the connections between the gates in the gate chip.

Now refer to FIG. 2. The time-delay switch includes: a button S1, a capacitor E1 for charging and discharging, a discharge resistor R, a gate chip IC1, and a transistor D1. In an embodiment, the gate chip is a 74HC14. The gate chip has an internal structure as shown in FIG. 3, which includes six integrated packaged NOT gates. The connections between the gates when used are as shown in FIG. 4. Particularly, a NOT gate A, a NOT gate B, parallel-connected NOT gates C and F, and parallel-connected NOT gates D and E are connected in series in an order. The input terminal of the gate chip is an input terminal of the NOT gate A, and the output terminal of the gate chip is output terminals of the parallel-connected NOT gates D and E. The gate chip 74HC14 has low power consumption and high input impedance, so even a capacitor with low capacity can make the discharge time long enough, which further lightens the weight of the auto-darkening welding lens. In a matter of course, 555 chips or other gates may be used.

The button S1 is connected at one of its terminals to a power supply terminal Vcc, and is connected at the other terminal to the capacitor E1. The capacitor E1 is connected in parallel to the discharge resistor R. The gate chip IC1 is connected at its input terminal to the voltage output terminal of the capacitor E1, and is connected at its output terminal to the base of the transistor D1 through a current limiting resistor R3. The transistor D1 is connected at its emitter to the ground. The LED is connected at its cathode to the collector of the transistor D1, and is connected at its anode to the power supply terminal Vcc. The power supply terminal Vcc is connected in parallel to a decoupling capacitor E2. The discharge resistor R includes two resistors R1 and R2 connected in parallel. An adjustable resistor would be an impractical solution, because the size of the lighting device has to be kept small. By using the two parallel-connected resistors, resistance of the discharge resistor can be conveniently selected so to set the discharge time. To start up the lighting device, the button S1 is pressed, then the power supply terminal Vcc charges the capacitor E1, the gate chip outputs a high voltage, the transistor D1 amplifies the current, and the LED is lit up. Meanwhile, the capacitor E1 discharges through the resistors R1 and R2; and when the voltage across the capacitor E1 is below a threshold at which the gate is on, the output of the gate is zero, the transistor D1 is off and the LED turns off, completing a lighting cycle. On one hand, this time-delay design is to save electricity; on the other hand, the weight of the welding mask has to be kept light because it is worn on the face, hence the size of the battery has to be kept as small as possible and the weight of the battery has to be kept as light as possible.

The invention claimed is:

1. An auto-darkening welding lens, comprising a window and a frame, the window comprising a filter and a liquid crystal plate that are stacked in an order, wherein:

the auto-darkening welding lens has a lighting device, the lighting device comprising a luminous element, a switch and a power supply that are electrically connected to form a loop, the luminous element being arranged on a face of the frame that is towards a welding object;

the switch is a time-delay switch;

the time-delay switch comprises a button, a capacitor for charging and discharging, a discharge resistor, a gate chip and a transistor, the button is connected at a terminal thereof to a power supply terminal and is connected at the other terminal thereof to the capacitor, the capacitor is connected in parallel to the discharge resistor, the gate chip is connected at an input terminal thereof to a voltage output terminal of the capacitor and is connected at an output terminal thereof to a base of the transistor, the transistor is connected at an emitter thereof to the ground, and the luminous element is connected at a cathode thereof to a collector of the transistor and is connected at an anode thereof to the power supply terminal.

2. The auto-darkening welding lens according to claim 1, wherein: the luminous element is a light-emitting diode.

3. The auto-darkening welding lens according to claim 1, wherein:

the gate chip is a 74HC14 chip.

4. The auto-darkening welding lens according to claim 1, wherein:

the gate chip comprises six NOT gates with a NOT gate, a NOT gate, parallel-connected NOT gates and parallel-connected NOT gates connected in series in an order, the input terminal of the gate chip is an input terminal of the NOT gate, and the output terminal of the gate chip is output terminals of the parallel-connected NOT gates.

5. The auto-darkening welding lens according to claim 1, wherein:

the discharge resistor comprises two resistors connected in parallel.

6. The auto-darkening welding lens according to claim 1, wherein:

the power supply terminal is connected in parallel to a decoupling capacitor.

* * * * *